United States Patent [19]
Rossignol

[11] Patent Number: 5,965,590
[45] Date of Patent: Oct. 12, 1999

[54] METHOD FOR TREATMENT OF OPPORTUNISTIC INFECTIONS WITH PHARMACEUTICAL COMPOSITIONS OF TIZOXANIDE AND NITAZOXANIDE

[76] Inventor: Jean-François Rossignol, 2650 Heron La. S., Clearwater, Fla. 34622

[21] Appl. No.: 08/887,809

[22] Filed: Jul. 3, 1997

Related U.S. Application Data

[63] Continuation-in-part of application No. 08/644,153, May 10, 1996, abandoned, application No. 08/847,130, May 1, 1997, Pat. No. 5,886,013, and application No. 08/852,447, May 7, 1997, said application No. 08/644,153, is a continuation-in-part of application No. 08/301,407, Sep. 8, 1994, Pat. No. 5,578,621, said application No. 08/847,130, is a continuation of application No. 08/388,855, Feb. 6, 1995.

[51] Int. Cl.$^6$ .................................................. A61K 31/425
[52] U.S. Cl. ............................................................. 514/371
[58] Field of Search .............................. 548/192; 514/371

Primary Examiner—Robert Gerstl
Attorney, Agent, or Firm—Pendorf & Cutliff

[57] ABSTRACT

Methods for treatment of *Cryptosporidium parvum*, *Isospora belli*, *Enterocytzoon bieneusi*, *Encephalitozoon intestinalis*, *Mycobacterium tuberculosis*, *Mycobacterium avium intracellulare*, *Pneumocystis carinii*, and *Toxoplasma gondii*, the methods comprising the administration of a pharmaceutical composition containing as active agent at least one compound selected the group consisting of a compound of formula I:

(I)

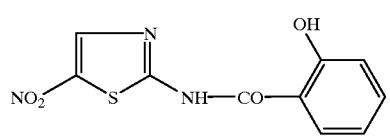

and a compound of formula II:

(II)

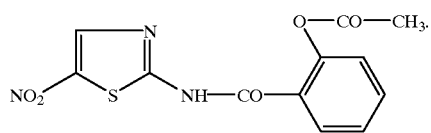

24 Claims, 9 Drawing Sheets

METHOD FOR TREATMENT OF OPPORTUNISTIC INFECTIONS WITH PHARMACEUTICAL COMPOSITIONS OF TIZOXANIDE AND NITAZOXANIDE

CONTINUATION DATA

This application is a continuation-in-part of U.S. application Ser. No. 08/644,153 filed May 10, 1996, abandoned, which is a continuation-in-part of U.S. application Ser. No. 08/301,407 filed Sep. 8, 1994 now U.S. Pat. No. 5,578,621; and a continuation-in-part of U.S. application Ser. No. 08/847,130 filed May 1, 1997 now U.S. Pat. No. 5,886,013, which is a continuation of U.S. application Ser. No. 08/383,855 filed Feb. 6, 1995; and a continuation-in-part of U.S. application Ser. No. 08/852,447 filed May 7, 1997.

BACKGROUND OF THE INVENTION

1. Field of the Invention

The present invention relates to a method for treatment or prevention of infections, and particularly opportunistic infections of one or more of *Cryptosporidium parvum, Isospora belli, Enterocytzoon bieneusi, Encephalitozoon intestinalis, Mycobacterium tuberculosis, Mycobacterium avium intracellulare, Pneumocystis carinii*, and *Toxoplasma gondii* in persons with compromised or suppressed immune systems, the method comprising administration of a pharmaceutical composition containing as active agent a compound selected fromthe group consisting of a desacetyl-nitazoxanide and nitazoxanide.

2. Description of the Related Art

There is an urgent need for the development of methods for treatment or prevention of a number of parasitic and bacterial infections prevalent in humans and animals, particularly in humans with compromised immune systems (AIDS, cancer patients, elderly, aging). Nitazoxanide, desacetyl-nitazoxanide and combinations thereof may be very useful in treating or preventing many of the most common "opportunistic" bacterial or parasitic infections in person with either competent or compromised immune systems.

*Toxoplasma gondii* is a protozoan and is among the most prevalent causes of latent infection of the central nervous system throughout the world. Infection occurs primarily via the oral route through ingestion of raw or undercooked meat or contact with cat excrement. Many healthy people are infected with the parasite, but usually the immune system keeps the organism under control. The most frequent symptoms include headache, confusion, fever, and focal neurologic deficits. *T. gondii* is also the most common opportunistic pathogen of the brain in AIDS patients. At present, toxoplasmosis is becoming an increasing problem not only because of AIDS, but also because of wider use of immunosuppressive drugs (e.g., as administered to organ-transplant patients). Toxoplasmosis is also a threat to the fetus and newborn infant, even in healthy persons without immune suppression.

Toxoplasmosis is usually treated with a combination of pyrimethamine and sulfadiazine (leucovorin must be given with the pyrimethamine). While the drugs are effective, they do not kill cysts of the parasite, so the treatment must be continued as a maintenance dose; often toxicity forces discontinuation of the drug, and relapses result. The statistics are not good, with reported death rates of about 70 percent in immunodeficient patients and median survival of four months.

Cryptosporidiosis is caused by the microscopic protozoan parasite *Cryptosporidium parvum*. Symptoms include profuse diarrhea, abdominal cramping, urgency, severe dehydration and weight loss. In persons with normal immune functions, the diarrhea caused by *C. parvum* may be intense and prolonged, but is self-limiting. In AIDS patients, cryptosporidial diarrhea poses a serious health risk, as the disease can be chronic, severe and often life-threatening. It is estimated that 15–20 percent of AIDS patients suffer from this condition. Up to now, there has been no consistently effective or approved therapy for cryptosporidiosis.

The most frequently identified pathogen in AIDS patients is *Enterocytozoon bieneusi*, a microsporidian parasite, which was found in nearly one-quarter of the patients. Smaller even than Cryptosporidium, it now appears that this tiny parasite, which can only be identified in biopsies of the small intestine or duodenum that are examined by electron microscope, may turn out to be the cause of a large proportion of the many unexplained cases of malabsorption, diarrhea and wasting seen in HIV-ill patients. *E. bieneusi* lives mainly inside small intestinal cells, but has also been reported as a cause of sinusitis. It causes a specific pattern of damage to mucuous membrane resulting in malabsorption and diarrhea, which both contribute to malnutrition. The dying cells appear to release the organism's tiny spores into the gut. There is no known treatment as yet.

Several other species of microsporidia infect HIV-positive patients, including *Encephalitozoon hellem* and *cuniculi*, and a new species designated *Septata intestinalis*. *Encephalitozoon hellem, cuniculi* and *Septata intestinalis* have produced disseminated infections with symptoms mainly in the sinus or eyes. A recent report describes several patients with symptomatic and asymptomatic pulmonary microsporidiosis resulting from *E. hellem*, and suggests that disseminated microsporidia infections are increasing in significance.

Infection with the parasite *Isospora belli* is clinically indistinguishable from cryptosporidiosis, but it can usually be treated with trimethoprim-sulfamethoxazole or other sulfa drugs. The organism is larger than *Cryptosporidium parvum* and can be identified with the same staining techniques. More common in tropical climates, *I. belli* has been reported in less than 1% of patients in the U.S., although its actual incidence is probably higher. While there have been no controlled trials of sulfa alternatives in treatment of Isospora, there are anecdotal reports of both success and failure with quinacrine, roxythromycin, metronidazole or nitrofurantoin.

*Pneumocystis carinii* has generally been classified as a protozoan parasite; some studies indicate it may be a fungus, with which it shares certain genetic sequences. *P. carinii* usually infects the lungs (*Pneumocystis Carinii* Pneumonia (PCP)), and more rarely infects extrapulmonary sites, including the lymph nodes, bone marrow, spleen, and liver. Symptoms include fever, dry cough, chest tightness, and difficulty breathing. Therapy is reported to be successful in about 40–60% of patients, with problems including drug toxicity particularly in immunocompromised patients. Among the many serious manifestations of human immunodeficiency virus (HIV) infection in children, PCP stands out because of its high incidence, unique age distribution, and frequent mortality. PCP is the most common serious opportunistic infection in children with HIV infection; the incidence of PCP among HIV-infected infants not receiving prophylaxis is estimated to be at least 12% in the first year of life. Many children die shortly alter PCP develops; one survey found that 31% of 300 children with PCP diagnosed in 1991 and 1993 died within 2 months of the PCP diagnosis.

Mycobacterium Avium Complex (MAC) refers to infections by a family of very similar mycobacterial organisms, *Mycobacterium avium* and *M. intracellulare*. These bacteria are ubiquitous in soil, food, and water. When MAC occurs in non-immunocompromised people, it usually causes infection in the respiratory tract. In patients with AIDS, MAC is frequently disseminated (disseminated MAC or DMAC). Almost any organ system can be involved, especially those with many mononuclear phagocytes (e.g., the liver, spleen and bone marrow). In a recent study, MAC bacterial was found in 43% of patients who survived for 2 years after an AIDS diagnosis. Signs and symptoms of DMAC are generally nonspecific, such as fever, night sweats, weight loss, weakness, and anorexia. Diarrhea, malabsorption, and abdominal pain may indicate gastrointestinal involvement; enlargement of the liver and spleen is common. No standard therapy has been established for disseminated MAC. Combinations of drugs are usually prescribed and, if successful, require that treatment be continued for life. In a recent open, randomized study, at 6 months, the success rate (defined as alive with decreased fever and negative blood cultures) was 28% for patients in a clarithromycin and clofazimine group and 46% in a triple combination group. A more effective treatment is urgently needed.

HIV-infected people are particularly susceptible to infection by *Mycobacterium tuberculosis*, and the course of the disease is accelerated. While extrapulmonary tuberculosis is unusual in non-HIV-infected patients, it frequently occurs in HIV-positive people. The lymphatic system is frequently involved. The classic symptoms of tuberculosis (cough, weight loss, fever, night sweats, fatigue) are often present. The CDC has released guidelines for the treatment of TB which address the growing prevalence of multi-drug resistant TB (MDR-TB). Mortality among AIDS patients with MDR-TB is very high (approximately 80%) and the disease progression is extremely rapid.

Accordingly, there is an urgent need for the development of a method of treatment of these infections so prevalent in, and threatening to, humans and animals.

SUMMARY OF THE INVENTION

The present invention is based on the surprising discovery that *Cryptosporidium parvum, Isospora belli, Enterocytzoon bieneusi, Encephalitozoon intestinalis, Mycobacterium tuberculosis, Mycobacterium avium intracellulare, Pneumocystis carinii,* and *Toxoplasma gondii* infections can be optimally and effectively treated, particularly in the immuno-compromised, by a method comprising administration of a pharmaceutical composition containing as active agent a compound selected the group consisting of desacetyl-nitazoxanide and nitazoxanide.

The pharmaceutical composition may be in a form suitable for oral administration, as a solid dosage form, a liquid suspension, or a paste.

The foregoing has outlined rather broadly the more pertinent and important features of the present invention in order that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other pharmaceutical compositions and methods for treatment for carrying out the same purposes of the present invention. It should also be realized by those skilled in the art that such equivalent formulations and methods do not depart from the spirit and scope of the invention as set forth in the appended claims.

BRIEF DESCRIPTION OF THE DRAWINGS

For a fuller understanding of the nature and objects of the present invention reference should be made by the following detailed description taken in with the accompanying drawings in which.

DETAILED DESCRIPTION OF THE INVENTION

Figure 1:
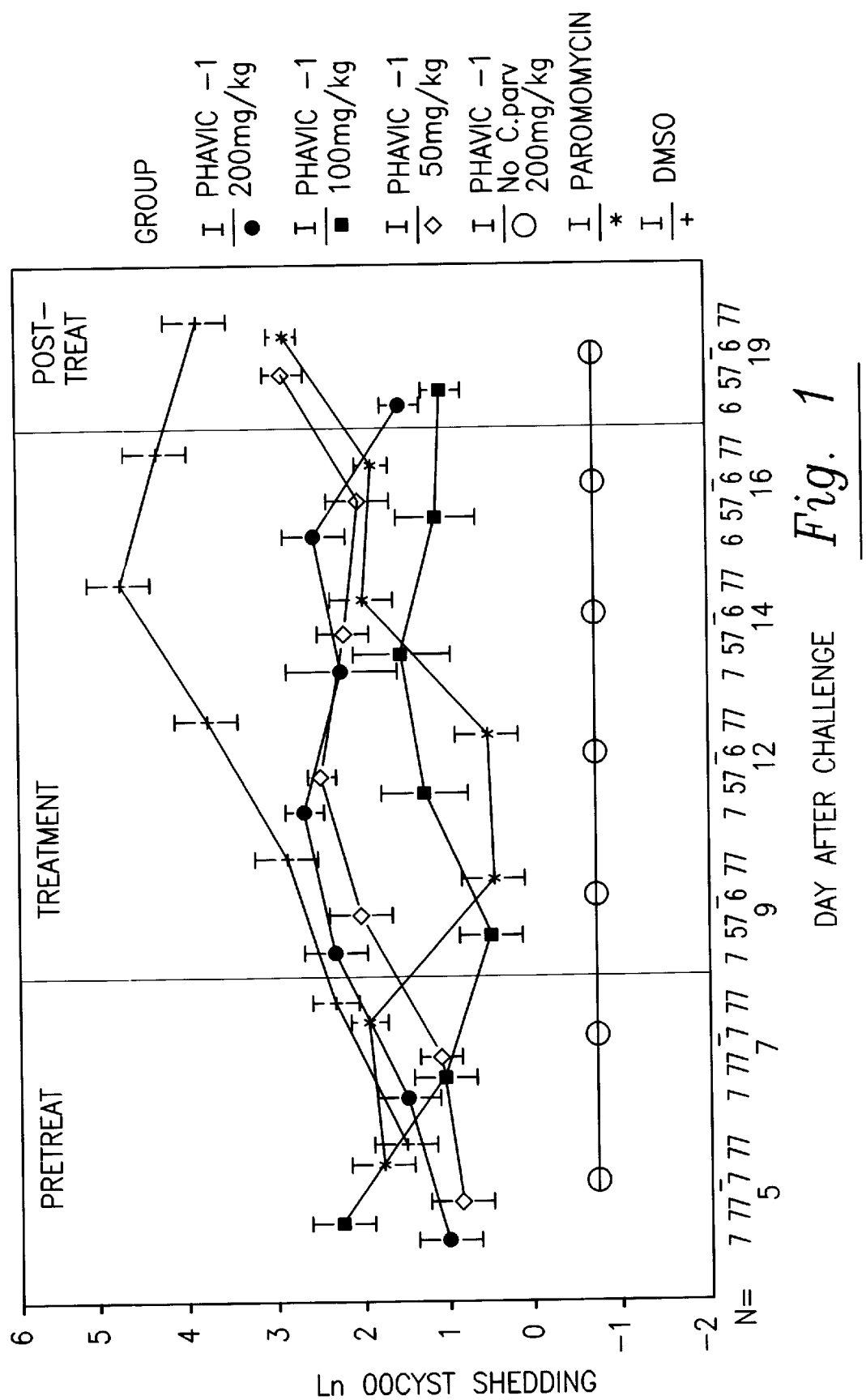
FIG. 1 shows a two way analysis of variance of the log oocyst shedding from 6 groups of weaned male SCID mice infected with *C. parvum*.
Figure 2:
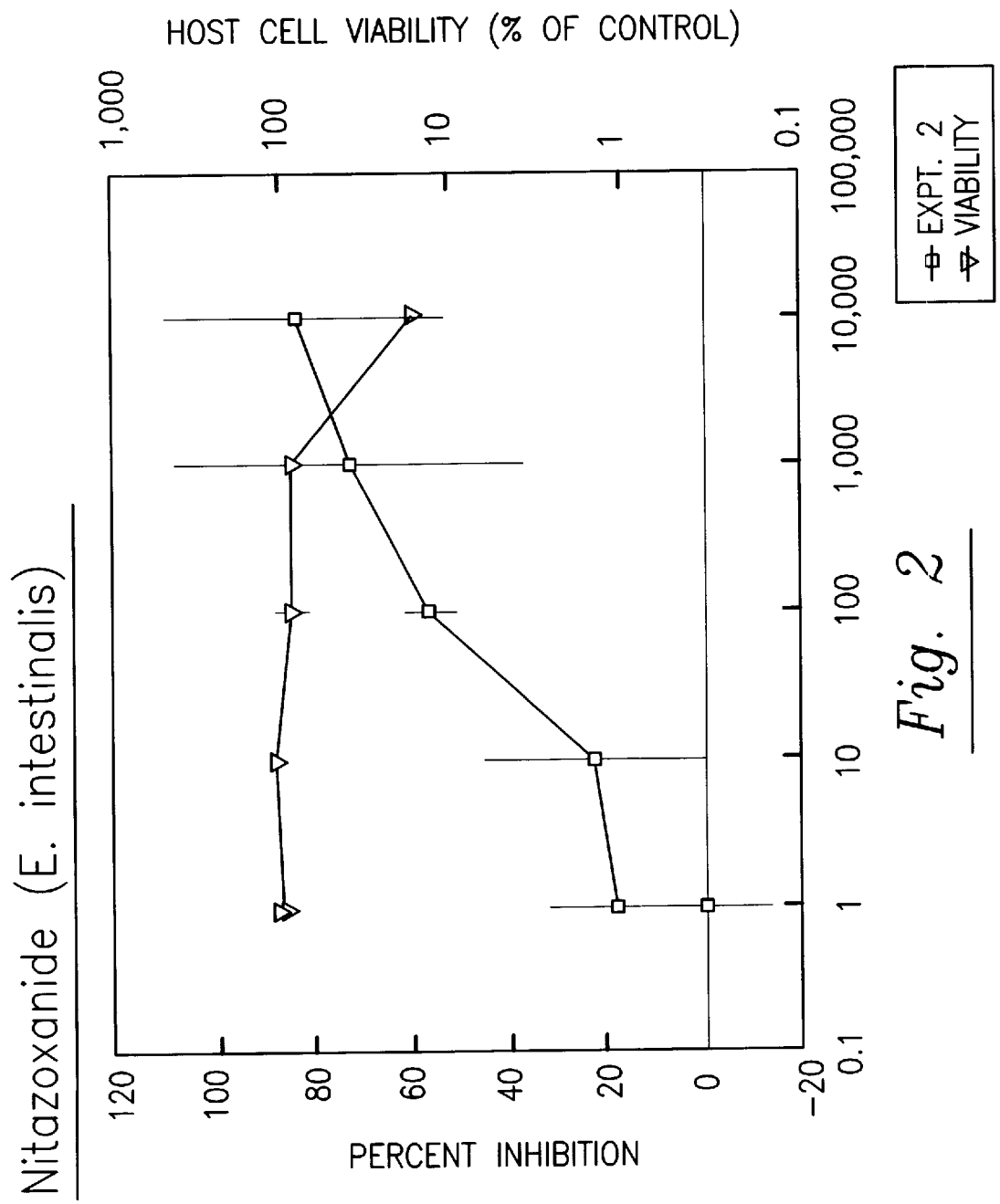
FIG. 2 shows percent inhibition and host cell viability of nitazoxanide against *E. intestinalis*.
Figure 3:
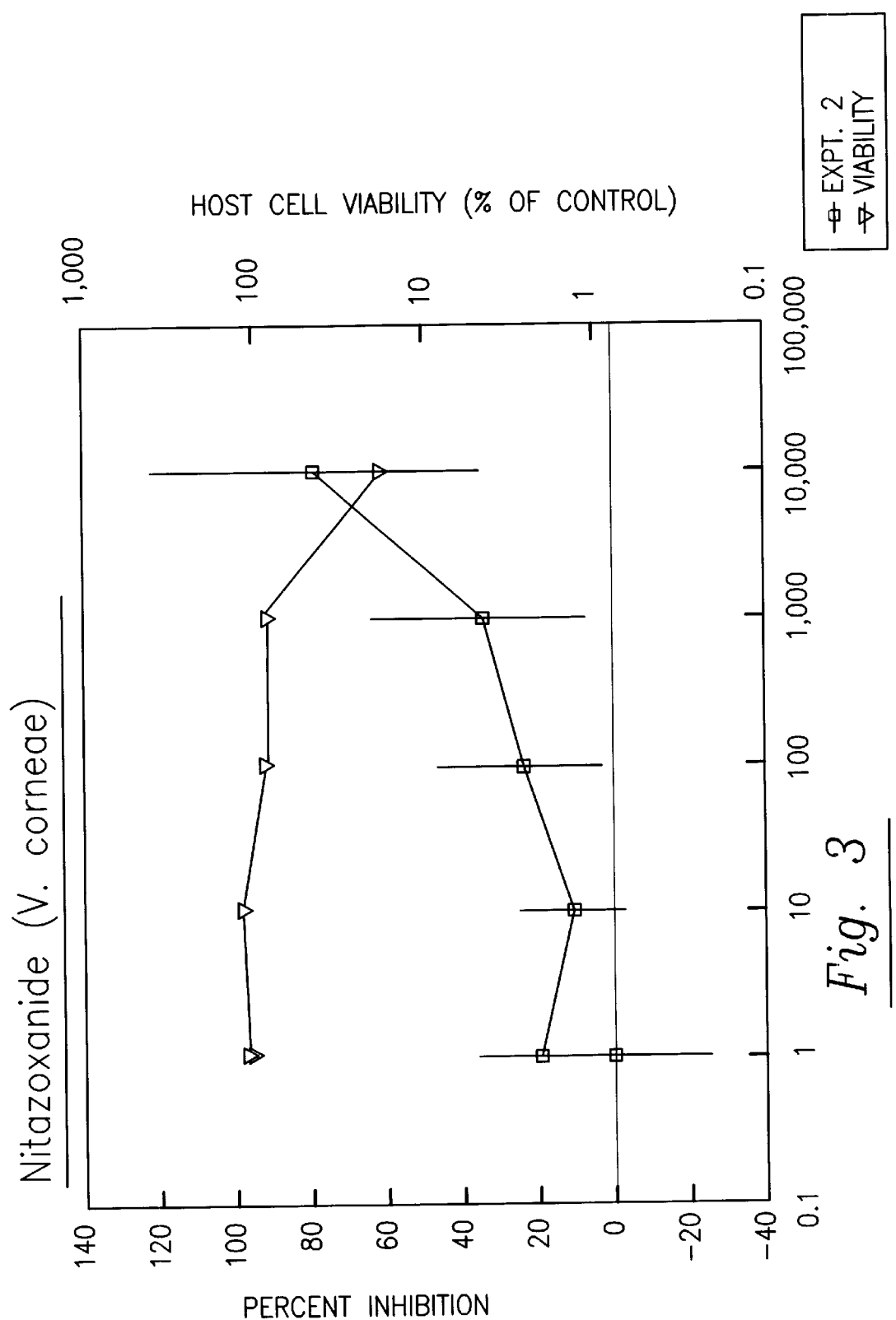
FIG. 3 shows percent inhibition and host cell viability of nitazoxanide against *V. corneae*.
Figure 4:
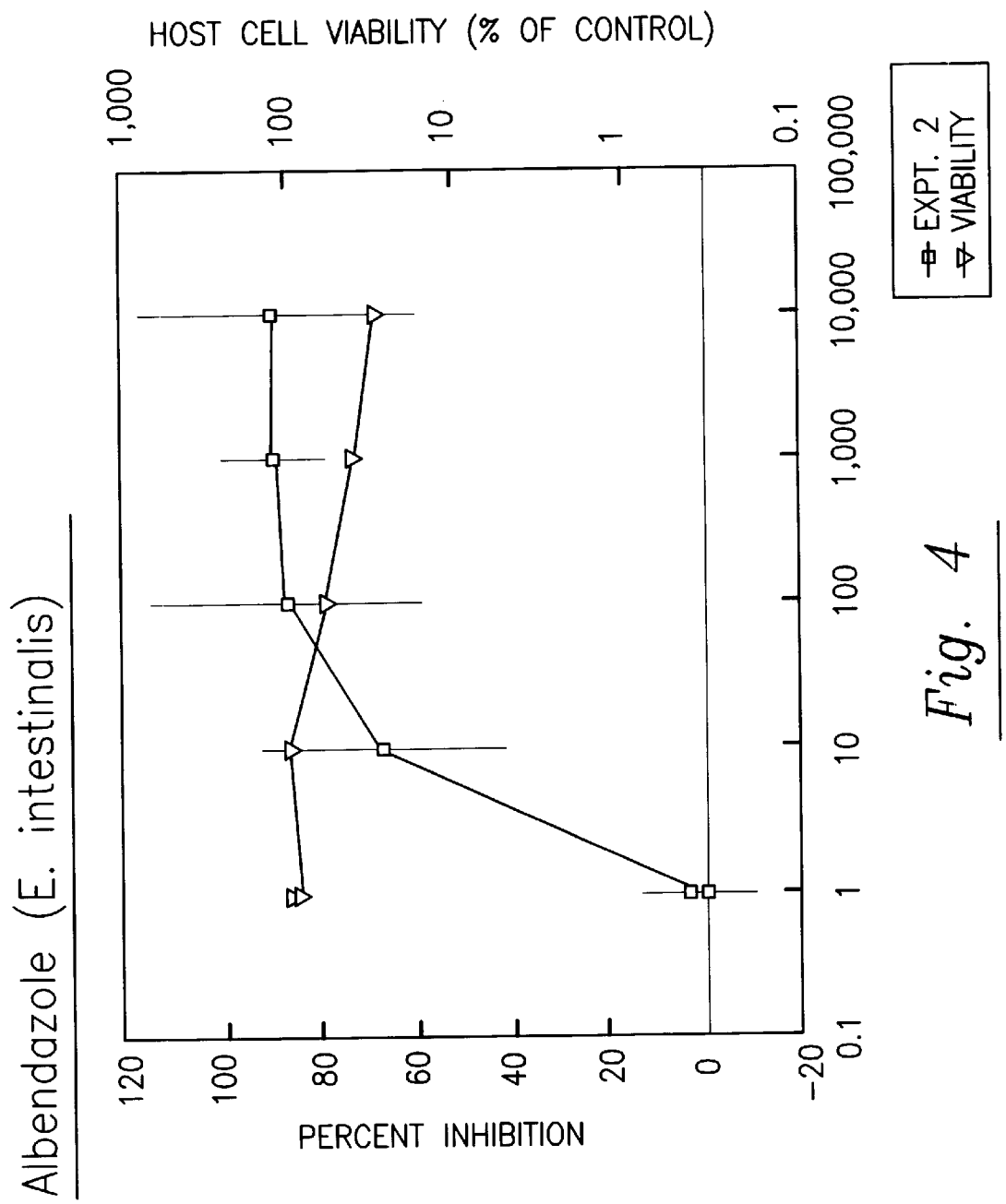
FIG. 4 shows percent inhibition and host cell viability of albendazole against *E. intestinalis*.
Figure 5:
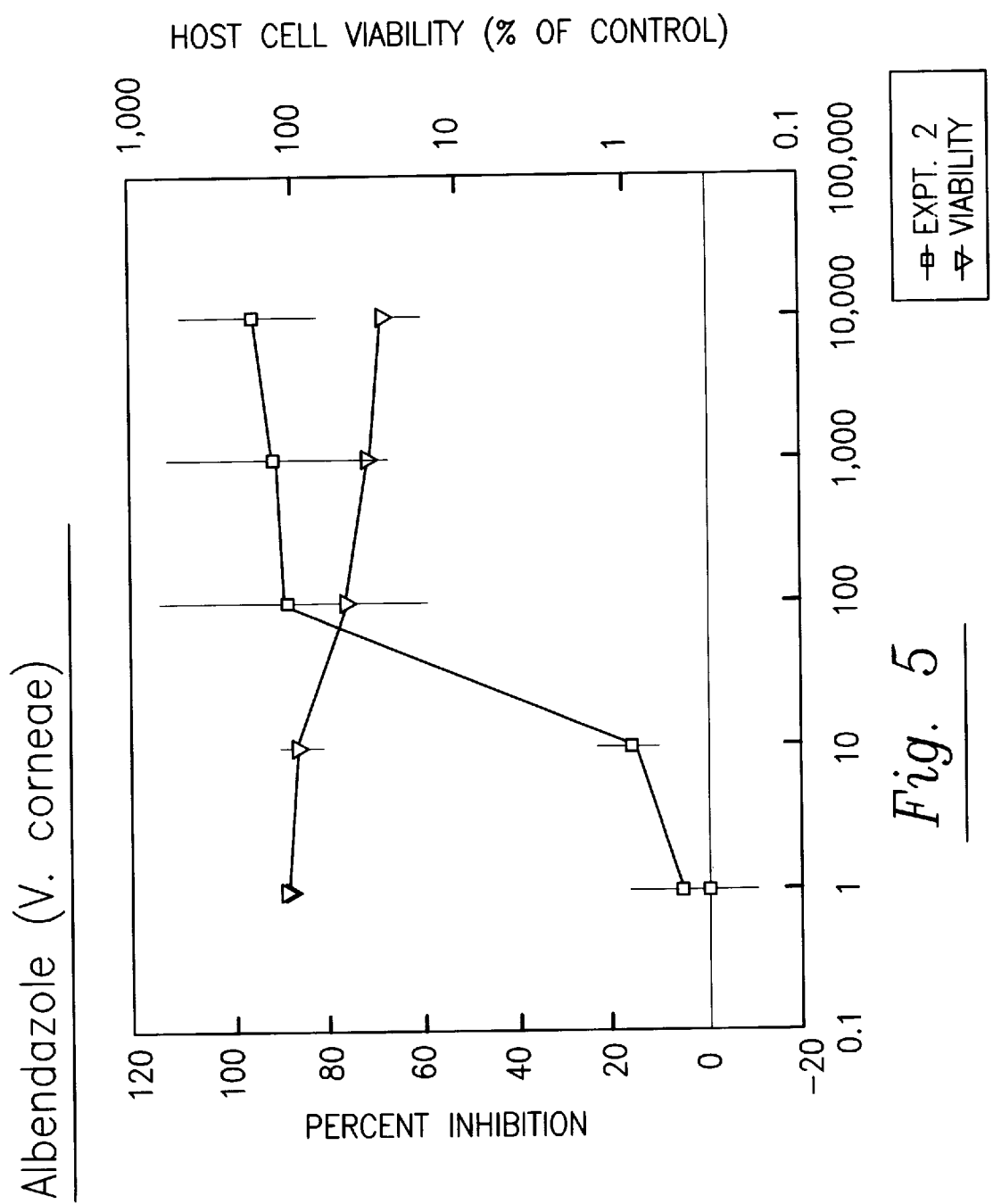
FIG. 5 shows percent inhibition and host cell viability of albendazole against *V. corneae*.

The method for treatment of *Cryptosporidium parvum, Isospora belli, Enterocytzoon bieneusi, Encephalitozoon intestinalis, Mycobacterium tuberculosis, Mycobacterium avium intracellulare, Pneumocystis carinii,* and *Toxoplasma gondii* infections of the present invention comprises administration of a pharmaceutical composition comprising, as active agent, a compound selected among the group consisting of desacetyl-nitazoxanide of formula I:

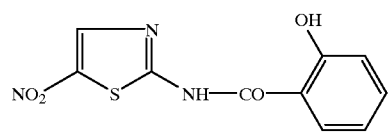

and nitazoxanide of formula II:

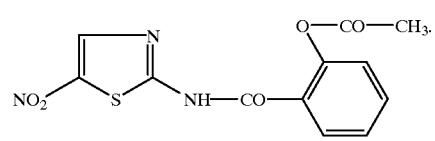

(II)

Nitazoxanide, the compound of formula II, sometimes referred to hereafter as NTZ or compound PH 5776, is the generic name for 2-(acetolyloxy)-N-(5-nitro 2-thiazoly) benzamide, a compound first synthesized by Rossignol and Cavier in 1975 and subsequently shown to have activity against a number of protozoan and helminthic pathogens. Nitazoxanide has a molecular weight of 307.2; it appears as odorless yellow granules with a melting point of 202–204° C.; it is very poorly soluble in water, ether and methyl benzene; poorly soluble in ethanol, chloroform and acetic acid; fairly soluble in dioxane and acetone and easily soluble in pyridine. Solubilisation in DMSO is recommended.

In 1980, Euzeby et al reported the cestocidal effect of a single oral dose of nitazoxanide against *Moniezia expansa, Avitellina centripunctata, Stilesia globipunctata* and *Thyzeniesia ovilla,* in sheep; *Dipylidium caninum* and *Taenia pisiformis* in dogs, and *Taenia taeniaeformis* in cats. In addition, when using repeated doses of the drug, efficacy against gastro-intestinal nematodes of dogs such as *Uncinaria stenocephala* and *Trichuris vulpis* was also observed. In 1982 Cavier and Rossignol reported the single dose activity of nitazoxanide against *Hymenolepis nana* in mice and the effect of repeated doses of the drug against *Syphacia obvelata* in mice. More recently Dubreuil et al. reported that nitazoxanide was also effective against Gram positive bacteria such as *Staphylococcus aureus* and facultative and obligate anaerobic Gram positive and Gram negate bacteria.

The preparation and certain uses of this compound are disclosed in U.S. Pat. No. 3,950,351, as well as in publications made by the present inventor.

Desacetyl-nitazoxanide, the compound of formula II, is sometimes referred to as tizoxanide or d-NTZ, and is a metabolite of nitazoxanide.

In WO 95/28393, the present inventor disclosed a method for the manufacture of pure compound of formula I, as well as the use of the composition containing a mixture of compounds of formula I and II.

The compound(s) of formula I and II may be administered in either a solid dosage form or an aqueous suspension, and it is preferred that the pharmaceutical composition contain the effective dose of the active agent in the form of solid particles having a particle size smaller than 200 $\mu$m and containing compound of formula I and/or compound of formula II, the mean particle size of the said active solid particles being greater than 10 $\mu$m as determined by a Coulter® Counter LS 100. This equipment uses laser light at 750 nm to size particles from 0.4 to 900 $\mu$m in diameter by light diffraction. The samples are measured in water with a small amount of Triton X-100 in order to increase the wettability and deflocculate the powder.

The solubility is 2 mg of nitazoxanide in 1 ml DMSO. Nitazoxanide is easily absorbed orally.

Advantageously, the mean particle size of the said active solid particles is between 10 and 100 $\mu$m, preferably between 20 and 50 $\mu$m. In accordance with a preferred embodiment of the composition, less than 10% of the said active solid particles has a particle size smaller than 5 $\mu$m.

The invention also relates to pharmaceutical compositions described above which contain advantageously at least one pharmaceutically acceptable acid. Examples of such acids are: citric acid, glutamic acid, succinic acid, ethanesulfonic acid, acetic acid, tartric acid, ascorbic acid, methanesulfonic acid, fumaric acid, adipic acid, malic acid and mixtures thereof. Citric acid is very appropriate. The presence of said acid improves the stability of the active agent or agents.

The ratio of the weight of pharmaceutically acceptable acid/the weight of said active solid particles is advantageously between 0.01 and 0.5, preferably between 0.03 and 0.2. Advantageously, the amount of acid is sufficient for adjusting the pH of the suspension between 2 and 6, preferably between 3 and 5, most preferably between 3.5 and 4.5.

The active agent or agents used in the solid dosage form or suspension is advantageously a mixture of solid particles of compounds of formula I and of formula II with a particle size smaller than 200 $\mu$m, the weight content of compound of formula II with respect to the weight of compounds of Formula I and of Formula II of said mixture being comprised between 0.5 and 20%, preferably between 0.5 and 10%.

Techniques for preparation of, and preferred examples of, solid and liquid dosage forms of the pharmaceutical composition are disclosed in WO/95/28393, the disclosure of which is incorporated herein by reference. The compositions contain advantageously a wetting agent and possibly a starch derivative such as those disclosed in U.S. Pat. No. 5,578,621, the content of which is incorporated herein by reference for disclosing possible wetting agents and starch derivatives. The wetting agent as described in U.S. Pat. No. 5,578,621 serves as a dispersing agent.

Such pharmaceutical compositions, either as solid or liquid dosage forms or as pastes or ointments, can optionally contain additional active agents such as antibiotics, antiviral agents or proton pump inhibitors. While it is not advantageous, it is also possible that such pharmaceutical formulations may contain active solid particles of compound of Formula I and/or compound of Formula II which are larger than 200 $\mu$m.

The compositions can contain excipients known as such for the purpose of preparing forms suitable for oral administration. The efficacy and the safety of the pharmaceutical compositions disclosed hereabove were excellent in animals and in humans.

The pharmaceutical compositions described are suitable for treating human and animal infections caused by *Cryptosporidium parvum, Isospora belli, Enterocytzoon bieneusi, Encephalitozoon intestinalis, Mycobacterium tuberculosis, Mycobacterium avium intracellulare, Pneumocystis carinii,* and *Toxoplasma gondii.*

EXAMPLE I

CRYPTOSPORIDIUM PARVUM

In a preliminary clinical trial, 30 AIDS patients with chronic cryptosporidial diarrhea were treated with oral nitazoxanide from 500 to 2000 mg daily. If the diarrhea continued, the patients received an additional four weeks of nitazoxanide, up to 2000 mg a day.

Twenty-eight people completed two or more weeks of therapy and 16 of those were evaluable for a therapeutic response by the eighth week of treatment. In this latter group, 12 persons had a 50 percent or greater reduction in daily bowel movement frequency and 10 individuals had a marked reduction or eradication of the parasite in the stool, with the organism becoming undetectable in four people. Six patients met both clinical and parasitological response criteria for benefit.

Patients who received higher daily doses of drug for longer periods of time were more likely to have a positive response.

An open-label study of nitazoxanide for AIDS-related cryptosporidial diarrhea documented decreased bowel movements among persons taking 500, 1000, 1500, or 2000 mg of the drug daily. Trial participants had a mean CD4+ count of 42 cells/mm$^3$ (range 0–303 cells/mm$^3$), a mean 6.7 bowel movements daily for an average 15 months, *Cryptosporidium parvum* oocysts in stool, and no other apparent enteric pathogens. Almost all participants had failed therapy with azithromycin or paromomycin.

After 23 weeks, 9 of 13 had a complete clinical response (one to three predominantly formed bowel movements daily), and 4 of 13 had a partial clinical response (at least a 50 percent decrease in daily bowel movements or a change in stool consistency so that at least 75 percent were formed). By the end of the study, 8 of 11 had completely eradicated the parasite and the other three had substantial reductions in oocyst levels. There was a trend toward better response with doses of 1000 mg daily or higher and with longer therapy. Two trial participants had urticarial skin rashes; more than 90 percent adhered to the study regimen for more than four weeks.

EXAMPLE II

CRYPTOSPORIDIUM PARVUM

In vitro Dose Information:

Nitazoxanide was dissolved in sterile dimethylsulfoxide (DMSO) and tested against intact *C. parvum* oocysts infected cell monolayers at concentrations of 100 μg/ml, 10 μg/ml/1 μg/ml and 0.1 μg/ml. A second trail was performed which tested nitazoxanide at the additional concentrations of 20, 2, 0.2 and 0.02 μg/ml. These concentrations were achieved by serial dilutions with complete DMEM medium to yield a final DMSO concentration of 0.5%. The medium control also contacted 0.5% DMSO.

The experiment used a cell culture of MDBKF5D2 Cells grown in 7 mm chambers, and as *Cryptosporidium parvum*: GCHI oocysts, $5 \times 10^4$ per well, and was conducted to compare paromomycin (positive control) against nitazoxanide (experimental drug). Materials included Immune Anti-*Cryptosporidium parvum* Sporozoite Rabbit Serum (0.1%) and Fluorescein-Conjugated Goat Anti-Rabbit Antibody (1%).

Toxicity Testing Assay:

200 μl of medium containing nitazoxanide at concentrations of 100, 10, 1 and 0.1 μg/ml and the proper controls were introduced into two wells of a 96 well plate containing confluent MDBKF5D2 cell monolayers and two wells without monolayers. The drug was incubated on the monolayers at 37° C. and 8% $CO_2$. At 24 hours (trial 1) and 48 hours (trial 2), MTS (Owen's solution) the PMS were added to each well at concentrations of 333 μg/ml and 25 μM respectively. The plate was returned to the incubator in the dark to develop for two hours. At two hours, 100 μl of each supernatant was transferred to a new microtiter plate and read in the ELISA reader at 490 nm. Results were recorded and analyzed. Percent toxicity was calculated by subtracting the mean optical density (OD) of the drug supernatants from the mean optical density (OD) of the medium control supernatants (no drug), dividing by the OD of the medium control and multiplying by 100.

$$\frac{OD \text{ medium} - OD \text{ drug}}{OD \text{ medium}} \times 100$$

Intact *C. parvum* Oocyst Assay:

5×104 *C. parvum* oocysts per well were incubated in nitazoxanide (100, 20, 10, 2, 1, 0.2, 0.1 and 0.02 μg/ml) at 37° C. (8% $CO_2$) on confluent MDBKF5D2 cell monolayers. The level of infection in each well was determined and analyzed by an immunofluorescence assay at 24 to 48 hours. Percent Inhibition was calculated by subtracting the mean parasite count/10 field in the drug test wells from the mean parasite count/10 fields in the medium control (no drug), dividing by the medium control count, and then multiplying by 100.

$$\frac{\text{Medium control count} - \text{Drug test count}}{\text{Medium control count}} \times 100$$

Results:

| Compound | Conc. | Mean (+SD)* | Percent Toxicity | Percent Inhibition |
|---|---|---|---|---|
| Trial 1: 24 hrs. | | | | |
| Infected Media | 0 | 983.5(±128.2) | 0 | 0 |
| Paromomycin | 2 mg/ml | 482(±47.1) | 23.8 | 51 |
| NTZ | 100 μg/ml | Lost | 88.1 | NA** |
| | 10 μg/ml | 55.5(±13.5) | 65.1 | 94.4 |
| | 1 μg/ml | 224.5(±28.5) | 8.3 | 77.2 |
| | 0.1 μg/ml | 474.5(±29.5) | 19.3 | 51.8 |
| Trial 2: 48 hrs. | | | | |
| Infected Media | 0 | 2231.25(+90.03) | 0 | 0 |
| Paromomycin | 2 mg/ml | 580(+33.42) | 40.8 | 74.01 |
| NTZ | 20 μg/ml | 68.75(+13.77) | 92.87 | 96.92 |
| | 2 μg/ml | 113.75(+21.36) | 24.93 | 94.90 |
| | 0.2 μg/ml | 1020(+158.48) | 16.56 | 54.29 |
| | 0.02 μg/ml | 1041(+191.46) | 21.23 | 53.33 |

*Parasite Count/10 Fields
**Not available due to toxicity

Impact of nitazoxanide on the intact *C. parvum* oocysts:

In trial 1, nitazoxanide at concentrations of 10, 1 and 0.1 resulted in parasite inhibition levels of 94.4, 77.2 and 51.8%, respectively, and cell toxicity levels of 65.1, 8.3 and 19.3% respectively. Although nearly complete inhibition of parasite infection occurred in 10 μg/ml, a high toxicity rating was evident. At 1 μg/ml of nitazoxanide, parasite inhibition and cellular toxicity compared favorably to paromomycin at a concentration of 2 mg/ml (77.2% parasite inhibition and 8.3% toxicity for nitazoxanide at 1 μg/ml compared to 51 parasite inhibition and 23.8% cell toxicity for paromomycin at 2 mg/ml).

In trial 2, the drug was modified to obtain better dose distribution with minimum toxicity. Consequently, the cultures remained viable for 48 hours instead of 24 hours as in trial 1. Incubation for 48 hours clearly resulted in higher relative cell toxicity as evident form examination of paromomycin in both trials. The 20 μg/ml concentration of nitazoxanide was still too toxic at 48 hours incubation although the cell monolayer appeared still intact. It is possible that high toxicity which must affect cell function also impacts parasite infection/development. At 2 μg/ml of nitazoxanide, there was a considerable inhibition of the parasite infection with relatively low cellular toxicity. Further dilutions also resulted in significant inhibition and low toxicity. At a drug concentration of 2 μg/ml, moderate cell toxicity and inhibitory activity of 94.90% indicates that nitazoxanide at 2 μg/ml is superior to paromomycin for in vitro *C. parvum* infection at 2 mg/ml (e.g. 1000 times higher concentration).

EXAMPLE III

CRYPTOSPORIDIUM PARVUM

In vitro Dose and Storage Information:

Stocks of nitazoxanide and desacetyl-nitazoxanide (NTZ and NTZdes) were tested against intact *C. parvum* oocysts and excysted sporozoite infected cell monolayers at concentrations 10, 1, 0.1 and 0.01 μg/ml. Each compound was dissolved in 100% dimethyl sulfoxide (DMSO) and diluted to the desired concentrations with sterile DMEM. Each concentration of nitazoxanide and the media controls contained 0.025% DMSO as a constant.

The experiment used a cell culture of MDBKF5D2 Cells grown in 7 mm chambers, and as *Cryptosporidium parvum*: GCH1 oocysts, 5×10$^4$ per well, and was conducted to compare paromomycin (positive control) against nitazoxanide (experimental drug). Materials included Immune Anti-*Cryptosporidium parvum* Sporozoite Rabbit Serum (0.1%) and Fluorescein-Conjugated Goat Anti-Rabbit Antibody (1%).

parasite count/field in the drug test wells from the mean parasite count/field in medium control (no drug), dividing by the medium control count and multiplying by 100.

$$\frac{\text{Medium control count} - \text{Drug test count}}{\text{Medium control count}} \times 100$$

Results:

| Drugs | Conc | Parasite | ±SD | Tox/OD | ±SD | % Inhib. | % Tox | Score |
|---|---|---|---|---|---|---|---|---|
| *C. parvum* Oocysts Assay (48 hr.) | | | | | | | | |
| Aqueous Media | 0 | 681.58 | ±271.02 | 2.024 | ±0.18 | 0 | 0 | 0 |
| Paromomycin | 2000 | 115.75 | ±44.65 | 1.219 | ±.009 | 83.02 | 39.79 | 2 |
| 0.025% DMSO Media | 0 | 628.50 | ±171.94 | 1.799 | ±1.45 | 0 | 0 | 0 |
| NTZ | 10 | 11.75 | ±7.33 | .413 | ±0.13 | 98.13 | 77.07 | 4 |
|  | 1 | 39.67 | ±13.13 | 1.618 | ±.326 | 93.69 | 10.09 | 1 |
|  | 0.1 | 643.42 | ±229.73 | 1.878 | ±.154 | ≦0 | ≦0 | 0 |
|  | 0.01 | 714.33 | ±194.79 | 1.617 | ±.072 | ≦0 | 10.12 | 1 |
| New NTZdes | 10 | 13.75 | ±6.66 | .337 | ±.005 | 97.81 | 81.27 | 4 |
|  | 1 | 39.92 | ±13.49 | 1.710 | ±.033 | 93.65 | 4.97 | 0 |
|  | 0.1 | 649.86 | ±152.19 | 1.506 | ±.119 | ≦0 | 16.29 | 1 |
|  | 0.01 | 749.33 | ±139.49 | 1.721 | ±.144 | ≦0 | 4.36 | 0 |

Conc. - μg/ml; Parasite - Mean parasite count/field (12 fields analyzed); % Inhib - Percent inhibitation of parasite infection; % Tox - Percent toxicity to cells by the drug.

Toxicity Testing Assay:

200 μl of medium containing nitazoxanide solution at the pre-mentioned concentrations and the proper controls were introduced into two wells of a 96 well plate containing confluent MDBKFD2 cell monolayers and two wells without monolayers. The drug was incubated on the monolayers at 37° C. and 8% $CO_2$. At 48 hours, MTS (Owen's solution) and PMS were added to each well at concentrations of 333 μg/ml and 25 μM respectively. The plate was returned to the incubator in the dark to develop for 2 hours. At 2 hours, 100 μl of each supernatant was transferred to a new microtiter plate and read in the ELISA reader at 490 nm. Results were recorded and analyzed. Percent toxicity was calculated by subtracting the mean optical density (OD) of the drug supernatants from the mean OD of the medium control supernatants (no drug), dividing by the OD of the medium control and multiplying by 100.

$$\frac{OD \text{ medium} - OD \text{ drug} \times 100}{OD \text{ medium}}$$

Cytotoxicity scores were assigned as follows: 0.5% toxicity=0, 6–25% toxicity=1, 26–50% toxicity=2, 51–75% toxicity=3 and 76–100% toxicity=–4. As a standard, cytotoxicity scores of 0 or 1 are to be considered acceptable levels of toxicity. Toxicity scores of 2, 3 or 4 are considered a high level or toxicity to the cell monolayer.

Intact *C. parvum* oocyst Assay:

5×104 *C. parvum* oocysts per well are incubated in the pre-mentioned concentrations of nitazoxanide at 37° C. (8% $CO_2$) on confluent MDBKF5D2 cell monolayers. The level of infection in each well was determined and computer analyzed by an immunofluorescence assay at 48 hours. Percent Inhibition was calculated by subtracting the mean It can be seen from the above that the Inhibitory activity of NTZdes, was the same as NTZ of Example II.

Both nitazoxanide and desacetyl nitazoxanide were equally effective in vitro against *Cryptosporidium parvum* when tested in parallel with 98 and 94% inhibitions obtained with 10 and 1 μg/ml for each compound respectively. For nitazoxanide 1 μg/ml was the lowest concentration giving more than 90% of inhibition while 50% inhibition could be obtained with lower concentrations of nitazoxanide such as 0.2, 0.1 and 0.02 μg/ml. In the same experimental condition paromomycin used as positive control was 2,000 times less effective with inhibitory concentrations ranging form 51 to 83% at a concentration of 2,000 μg/ml.

EXAMPLE IV

CRYPTOSPORIDIUM

Treatment of *Cryptosporidium parvum* for 10 days was done in scid mice I accordance with a conventional acute Cryptosporidium infection model using the control drug paromomycin. A maximum dose of 200 mg/kg/day was chosen.

The experiment involved C.B-17 scid mice, males, 3 weeks of age. The *Cryptosporidium parvum* was GCH1 oocysts, 10$^7$/mouse orally. 1 mg/mouse IP XMG1.2 (a-IGNg) was administered 2 hours before infection (diluted in sterile PBS).

Preparation of drug(s) (diluent, preparation, concentration, administration, storage):

1. Experimental Drug A: nitazoxanide.
   Preparation: Dissolved in dMSO
   Concentration: 200 mg/kg/day
   100 mg/kg/day
   50 mg/kg/day Administration: Oral, 2 divided doses of 30 ml each per day Storage: 4° C.

2. Paromomycin (=control drug): Rehydrate in sterile PBS, oral administration 2000 mg/kg/day administered orally in 2 doses of 30 ml each.

Oocyst shedding was monitored 3 times per week, beginning day 4 after challenge. Weight was measured each week. Toxicity was monitored daily. Histologically, necropsy was performed the day after challenge, and tissues analyzed were the pyloric region of the stomach, the mid small intestine, the ileum, cecum, proximal colon, and liver/gall Bladder.

Mice were distributed into 7 groups of 7 mice with equivalent total body weights. For priming, 1 mg XMG1.2 was administered to each mouse 2 hours prior to infection.

The following table shows challenge and treatment data:

| Group | No. Mice | XMG1.2 | C. parvum GCH1 Oocysts | Date/dose (mg/kg/day) | Treatment start (day of challenge) | Treatment end (day of challenge) | Euthanize (day of challenge) |
|---|---|---|---|---|---|---|---|
| 1 | 7 | yes | $10^7$ | nitazoxanide 200 mg/kg | day 6 | day 15 | day 20 |
| 2 | 7 | yes | $10^7$ | nitazoxanide 100 mg/kg | day 6 | day 15 | day 20 |
| 3 | 7 | yes | $10^7$ | nitazoxanide 50 mg/kg | day 6 | day 15 | day 20 |
| 4 | 7 | yes | — | nitazoxanide 200 mg/kg | day 6 | day 15 | day 20 |
| 5 | 7 | yes | $10^7$ | paromomycin 2000 mg/kg | day 6 | day 15 | day 20 |
| 6 | 7 | yes | $10^7$ | DMSO | day 6 | day 15 | day 20 |

Results

Oocyst shedding from 6 groups (7 mice each) of weaned male C.B=−17 SCID mice infected with $10^7$ oocysts of the GCH1 isolate. All mice received a single intraperitoneal injection of 1 mg XMG1.2 Mab 2 hours prior to oral challenge with C. parvum. Drug treatment began on day 6 of infection and continued for 10 days. Nitazoxanide was dissolved in DMSO and treatment were administered as follows: Group 1=200 mg/kg/day of nitazoxanide; Group 2—100 mg/kg/day of nitazoxanide (Phavid-1); Group 3=50 mg/kg/day of nitazoxanide (Phavic-1); Group 4=200 mg/kg/day of nitazoxanide (Phavic-1) uninfected control group for evaluating nitazoxanide (Phavic-1) toxicity; Group 5=2000 mg/kg/day of paromomycin (positive control drug); Group 6 served as the placebo control group and received 30 μl of DMSO orally two times per day. All treatments were administered orally in two divided odes per day with all mice monitored for an additional 5 days after the end of treatment.

The results are shown in FIG. 1. A two-way Analysis of Variance of the log oocyst shedding, with Day and Group as factors was run for each of the 3 phases:

Pre-Treatment Phase (Day 5 & &): significant difference between Groups (P=0.018). Newman-Keuls test shows (at P=0.05) that the Groups are indistinguishable with the exception of the DMSO Group, which differed significantly from every other Group.

Treatment Phase (Day 9 to 16): significant difference between groups (P<0.001). Newman-Keuls test shows (at P-0,05) that all groups differ except nitazoxanide 100 mg/kg/day and paromomycin 2000 mg/kg/day which are indistinguishable, and nitazoxanide 200 mg/kg/day and nitazoxanide 50 mg/kg/day which are indistinguishable.

Post-treatment Phase (Day 10): significant difference between Groups (P<0.001). Newman-Keuls test shows (at P=0.05) that all Groups differ except nitazoxanide 50 mg/kg/day and paromomycin 2000 mg/kg/day which are indistinguishable and nitazoxanide 200 mg/kg/day and 100 mg/kg/day which are indistinguishable.

It can be concluded that nitazoxanide at a daily dose of 100 mg/kg/day for ten consecutive days was as effective as paromomycin at a daily dose of 2000 mg/kg for ten consecutive days in reducing the daily oocysts shedding and the extent of the mucosal infections in experimentally infected SCID mice with Cryptosporidium parvum.

EXAMPLE V

E. INTESTINALIS AND V. CORNEA

RK-13 cells (rabbit kidney cell line) were added to 24-well culture plates at a concentration of 2.6×105 cells per well (1.0 ml medium; RPMI 1640 with 2 mM L-glutamine and 5% heat-inactivated fetal bovine serum). Dishes were incubated at 37° C. in a $CO_2$ incubator overnight at which time the wells were confluent (with one doubling, would estimate $5\times10^5$ cells per well).

Septata intestinalis (tissue culture-derived) organisms were added to the host cells at a 3:1 ratio compared with the estimated host cells or at $15.\times10^6$ organisms per well. This ratio resulted in approximately 50% of the host cells becoming infected).

Drugs were dissolved in DMSO, water or methanol (depending on solubility) to generate stocks of 1.0 mg/ml. Stocks were stored at −70° C. Dilutions used in experiments are made in complete tissue culture medium. All dilutions are tested in triplicate well.

Medium is replaced every three-to-four days (containing freshly-diluted drugs).

On day six (after adding parasites and drugs), the cells are examined for toxicity. Control cells given drugs but no parasites are examined for confluency, morphology of cells, and presence of dead or floating cells. Cells incubated with parasites only are examined to confirm that parasites are infectious (i.e. presence of parasitophorous vacuoles). Cells incubates the parasites and drugs are evaluated for host cell toxicity and relative numbers of parasitophorous vacuoles (i.e. high, medium, or low).

On day ten, 100 μl of 100 SDS (0.50% final concentration) was added to the culture wells to disrupt host cell membranes and cause release of the microsporidia. The total number of parasites present in each well was determined by counting an aliquot on a hemacytometer. Results are expressed as percent inhibition (relative to infected cells given no drug).

The results are shown in FIGS. 2–5.

EXAMPLE VI

TOXOPLASMA GONDII

Nitazoxanide and desacetyl nitazoxanide were tested against parasites, and more specifically, RH strain of *Toxoplasma gondii*, maintained by serial passages in mice. Cell cultures of MRC5 fibroblasts (Bio-Merieux, France) cultured in 96-well microplates were inocultated with *T. gondii*. 200 fresly harvested tachyzoites were added into each culture well, except in 8 control wells (negative controls). After 4 hours of incubation, drug dilutions were added into the cultures.

Nitazoxanide (NTZ) and desacetyl nitazoxanide (DNTZ) were tested at concentrations ranging between $8.10^{-4}$ and 40 mg/L. Drugs were initially dissolved in DMSO, at a concentration of 2 mg/mL, then serial dilutions were prepared in the culture medium. No precipitate was observed.

Drug dilutions were added into the cultures (8 wells for each dilution) then culture plates were incubated for 72 hours. Cultures were then fixed with cold methanol. Assessment of growth of *T. gondii* was performed buy ELISA using a peroxydase labeled rabbit anti *T. gondii* antibody. Optical density values were recorded for each well.

Resuts are presented by plotting the OD values obtained for each culture well, vs the concentration of the drug in the culture. Statistical analysis consisted in regression analysis with 95% confidence interval and determination of dose-response curves, from the OD values generated for each drug.

One plate was stained with Giemsa to examiner the cytopathic effect in the cultures.

Three separate experiments were realized. In each experiment, two culture plates were used for each compound; in each culture plate, 8 replicate wells were used for each drug concentration.

Figures 6A, 6B:
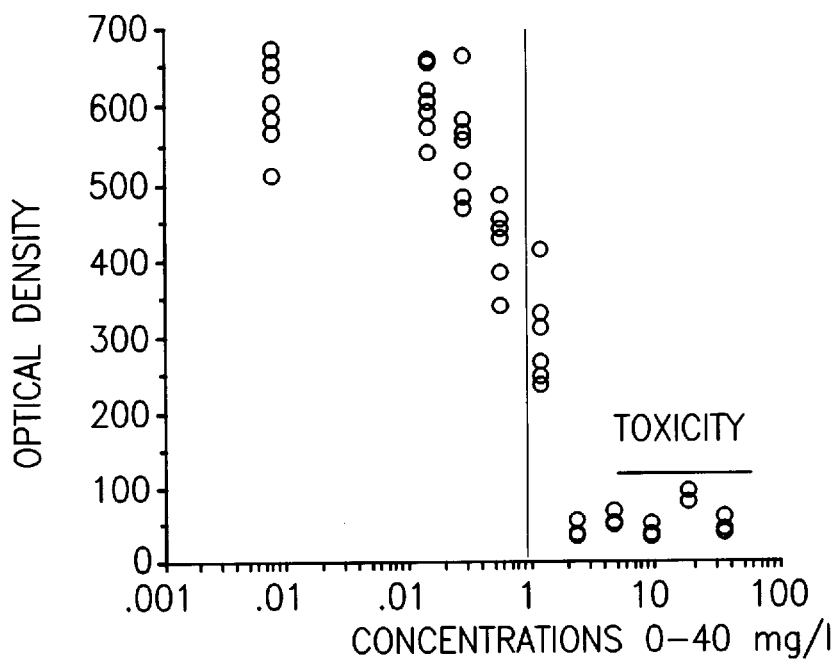
FIGS. 6 and 7 show a plot of OD values obtained for each *T. gondii* culture well, vs the concentration of the drug in the culture.
Figure 6C:
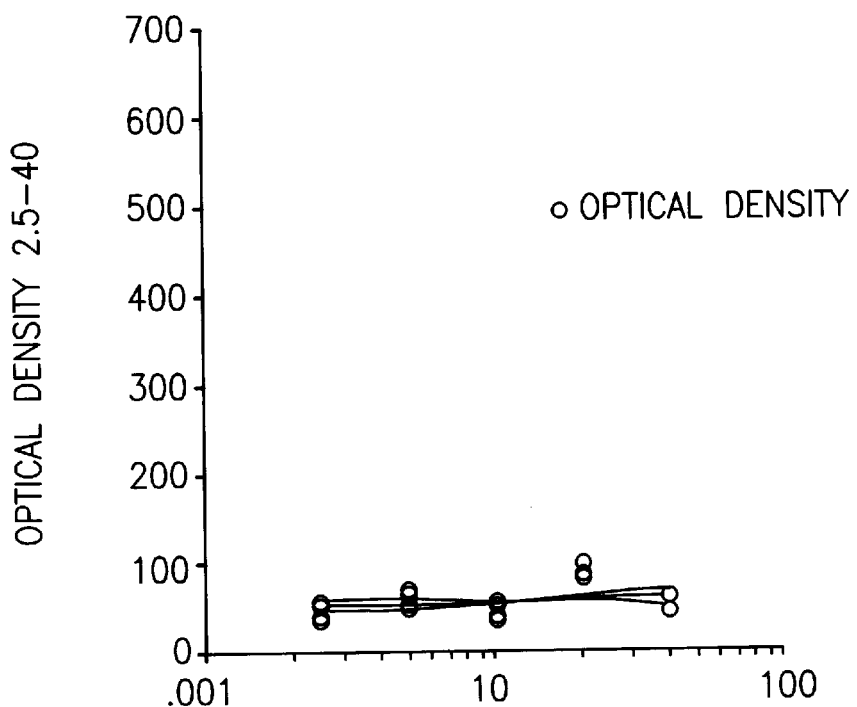

Results:

Similar results were obtained in the three sets of experiments. Graphic representations of the results of one representative experiment for each drug are shown on FIGS. 6 a,b,c and 7 a,b,c.

Nitazoxanide (FIGS. 6 a,b,c):

No inhibitory effect was noted for concentrations ranging between $10^{-4}$ mg/l and 0.3 mg/L. A significant effect was noted for concentration $\geq 0.6$ mg/L, with a complete inhibition of Toxoplasma growth for concentrations $\geq 2.5$ mg/L. However, a marked toxicity was noted on the cell monolayer for concentrations $\geq 2.5$ mg/L.

Microscopic examination of the monolayer showed that NTZ, at a concentration of 1.25 mg/L induced cytopathic effect on the parasitized cells, with enlargement of the parasitophorous vacuole and reduction of the number of the intra-celular parasites. From regression analysis, the 50% inhibitory concentration could be estimated at 1.2 mg/L.

Figure 7A:
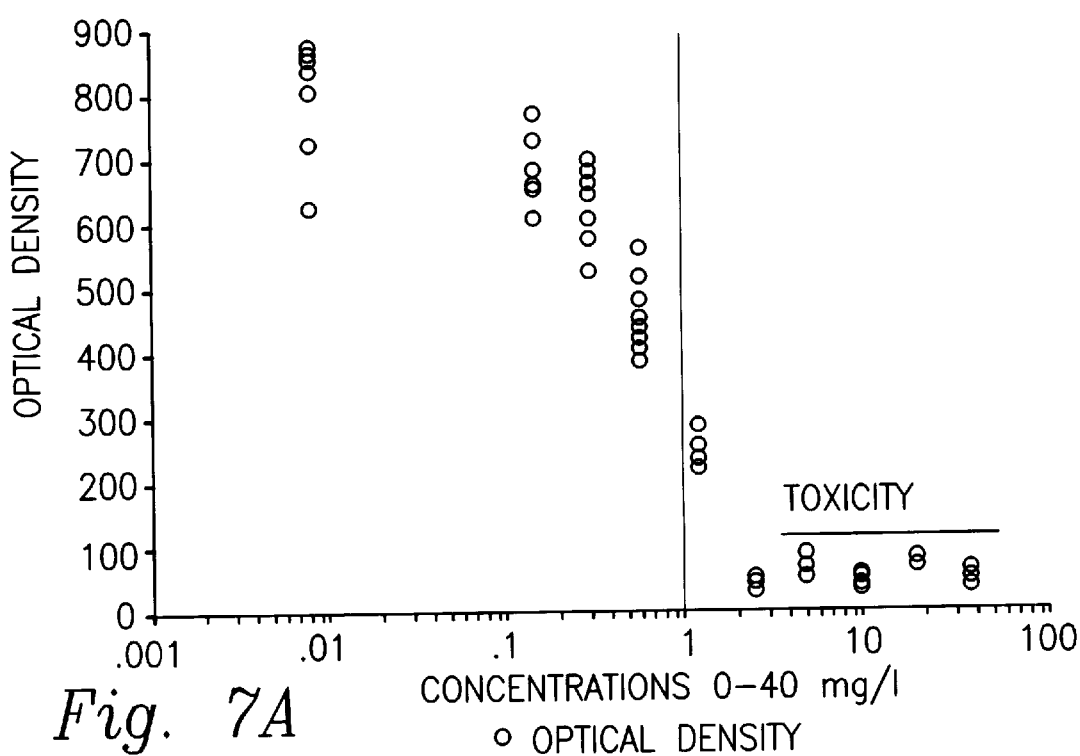
Figure 7B:
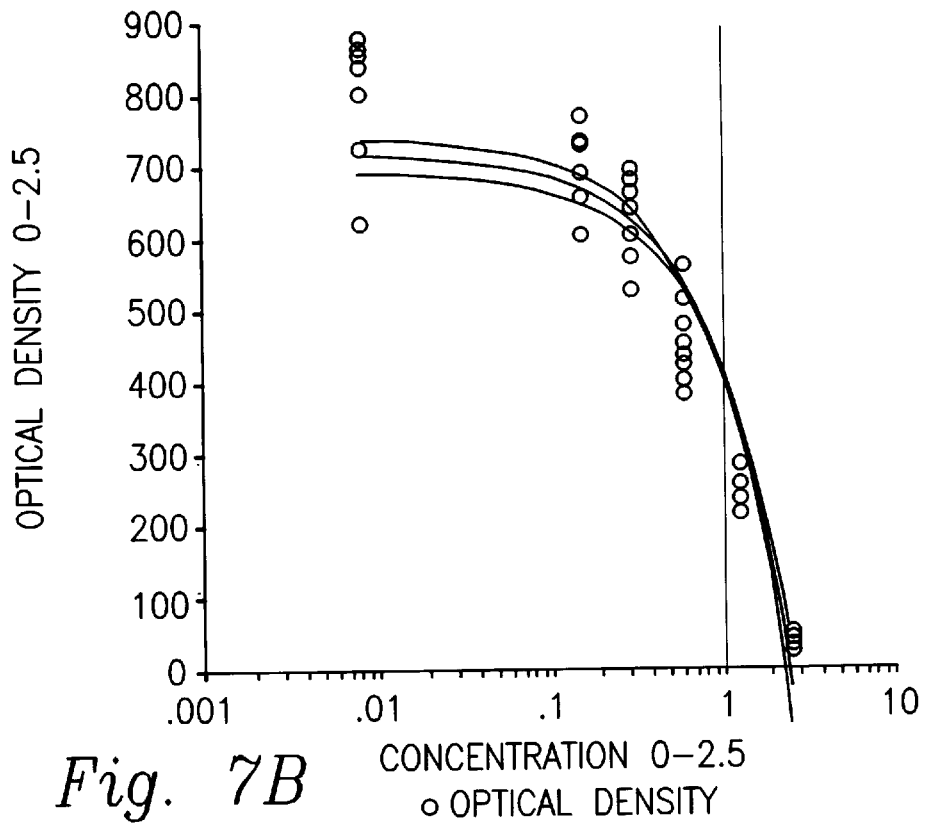
Figure 7C:
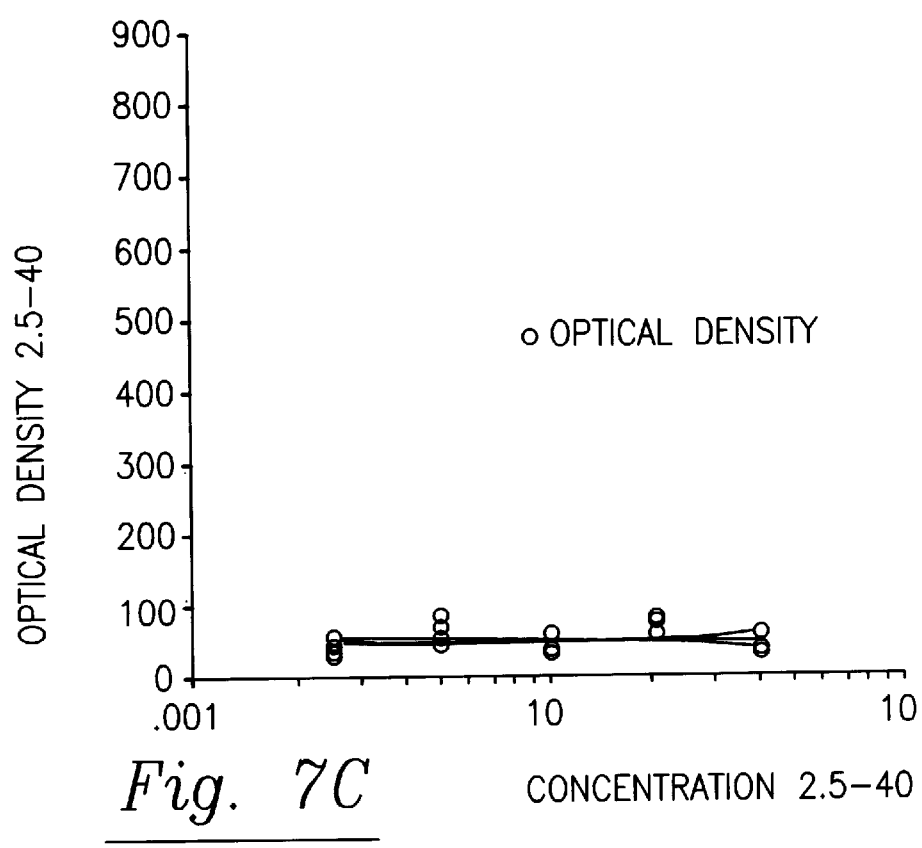

Deacetyl nitazoxanide (FIGS. 7 a,b,c):

Similar results were obtained with deacetyl nitazoxanide: no effect for concentrations ranging between $10^{-4}$ mg/L and 0.3 mg/L, inhibition for concentration $\geq 0.6$ mg/L, and marked toxicity for concentration $\geq 2.5$ mg/L. The 50% inhibitory concentration could be estimated at 1.2 mg/L.

The results obtained were reproducible over three separate experiments, with assessment of the drug inhibitory effect on repeated cultures for each drug concentration.

For both NTZ and deacetyl NTZ, a marked inhibition of Toxoplasma growth could be observed at concentrations of approximately 1.2 mg/L, with alteration of the parasitophorous vacuole but no marked alteration of the parasite itself.

These results indicate that these drugs have good activity against *T. gondii*, and that a therapeutic effect can be expected in vivo based on obtaining a concentration of approximately 1 mg/L in serum or tissues.

EXAMPLE VII

MYCOBACTERIA

Nitazoxanide was found to have antimicrobial activity against TB organisms. The following table shows an assay for MIC of nitazoxanide and tizoxanide against *Mycobacterium intracellular* by agar dilution technique. These results are based upon several experiments, each of which took about 3 weeks for the agar dilution method with Middlebrook agar. The data obtained indicate that nitazoxanide has an MIC against the Mycobacteria of 2 µg/ml and tizoxanide has an MIC of 4 µg/ml, using a standard strain of *Mycobacteriun intracellular* from ATCC, using the standard agar dilution assay.

| MICs of Nitazoxanide and tizoxanide to *Mycobacteia intracellulare* | |
|---|---|
| | MIC |
| Nitazoxanide | 2 µg/ml |
| Tizoxanide | 4 µg/ml |

*MICS were determined by standard agar dilution using Middlebrook 7H11 agar for 3 weeks. *M. intracellular* ATCC 13950, a standard strain, was used for this experiment.

Figure 8:
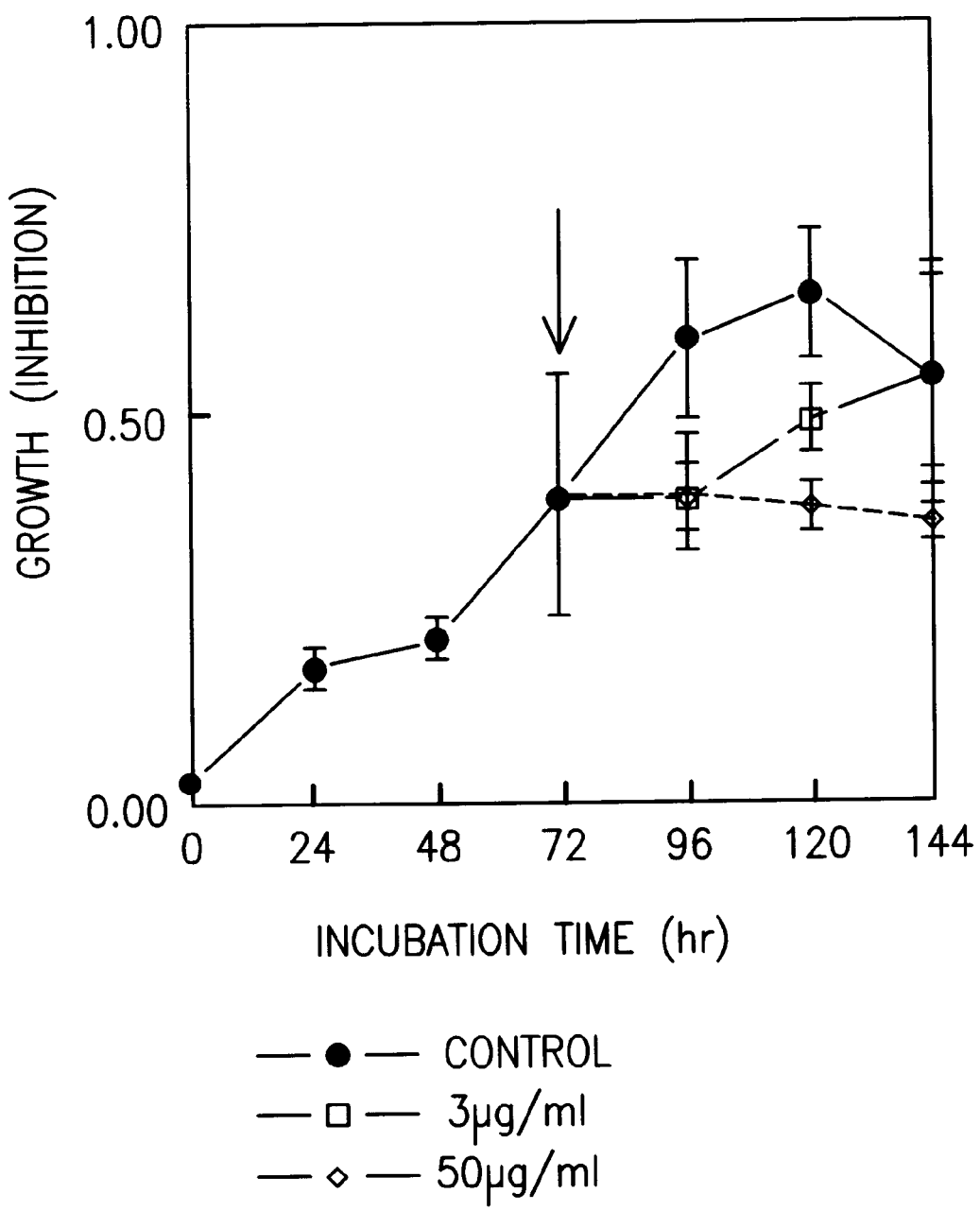
FIG. 8 is a chart based upon the assay for nitazoxanide effectiveness against mycobacteria growing in a liquid broth.

FIG. 8 is a chart based upon the assay for nitazoxanide effectiveness against mycobacteria growing in a liquid broth. We used the MTS colorimetric assay which permits us to determine growth in 4 hours rather than 3 weeks as with the agar counting method. As can be seen from the data in FIG. 8, when nitazoxanide was added at the 72 hr after culture was initiated, there was an immediate effect on continued growth as compared to the growth in control medium alone. The 3 µg/ml dose of nitazoxanide stops growth for the next 24 hrs and then there is a slow growth afterwards for the next 2 days. The 50 µg/ml dose was completely bacteriostatic throughout the 144 hours of the culture.

EXAMPLE VII

The effect of nitazoxanide was tested against *Cryptosporidium parvum* in experimentally infected mice. Nitazoxanide was supplied by Romark Laboratories, L.C. in Tampa, Fla.

The total human dose (1 g/day for 7 days i.e. 7 g) was modified for use for mice according to Paget and Barnes. The human dose was multiplied by 0.0026 for mice (weighing approximately 20 grams) to obtain he total amount of the drug needed for each host morning and evening for 7 consecutive days. Each mouse received 2.6 mg/day (7000 mg×0.0026/7). The doses were administered by mouth using a plastic syringe equipped with around tip needle.

Twenty (20) 2-day old suckling mice were infected by oral administration of 100,000 oocysts of *Crytospordium parvum* obtained from infected calves. Before being administered to mice, the oocysts were concentrated using a sugar solution according to the technique described by Fayer & Ellis. Rectal swabs from each mouse were obtained and examined daily using the modified Niehl-Neelsen staining technique described by Graczyk et al. Oocysts shedding appeared in feces 2 days after the oral infection of the animals. On the third day following infection of the animals, 10 mice received 1.3 mg of nitazoxanide, morning and evening, for 7 consecutive days while the 10 remaining mice were kept as untreated controls. Rectal swabs were obtained daily for each of the 7 days of treatment and for each of the 7 days following the end of treatment. The oocysts were suspended in oil and counted per 100 fields under a microscope.

Results:

The results shown in the following Table clearly indicate that nitazoxanide administered at a daily dose of 2.6 mg/day for 7 consecutive days was effective against *Cryptosporidium parvum* in reducing the number of oocysts in the feces of the infected mice when compared to the control animals. The test drug decreased the oocysts shedding in 6 of the 10 treated mice at the end of the third day of treatment. At the end of treatment of Day 7, there was a complete reduction of the oocyst shedding, all treatment animals having negative fecal examination when compared to untreated control mice. This effect lasted at least for 7 days after treatment as shown by negative examinations observed on days 3 and 7 after the end of treatment.

NO. OF OOCYST DETECTED PER OIL IMMERSION FIELD

| Mice No. | At 3$^{rd}$ day of treatment | | At last day of treatment | | At 3$^{rd}$ day post-treatment | | At 7$^{th}$ day post-treatment | |
|---|---|---|---|---|---|---|---|---|
| | Control group | Treated group | Control group | Treated group | Control group | Treated group | Control group | Treated group |
| 1 | 3.0 | 0.0 | 5.0 | 0.0 | 4.0 | 0.0 | 2.0 | 0.0 |
| 2 | 4.0 | 0.0 | 4.0 | 0.0 | 3.0 | 0.0 | 1.0 | 0.0 |
| 3 | 6.0 | 0.0 | 5.0 | 0.0 | 4.0 | 0.0 | 0.5 | 0.0 |
| 4 | 3.0 | 2.0 | 3.0 | 0.0 | 2.0 | 0.0 | 1.0 | 0.0 |
| 5 | 5.0 | 2.0 | 3.0 | 0.0 | 3.0 | 0.0 | 0.5 | 0.0 |
| 6 | 3.0 | 0.0 | 4.0 | 0.0 | 5.0 | 0.0 | 2.0 | 0.0 |
| 7 | 3.0 | 0.0 | 5.0 | 0.0 | 4.0 | 0.0 | 1.0 | 0.0 |
| 8 | 5.0 | 1.0 | 5.0 | 0.0 | 1.0 | 0.0 | 0.5 | 0.0 |
| 9 | 3.0 | 3.0 | 3.0 | 0.0 | 2.0 | 0.0 | 1.0 | 0.0 |
| 10 | | 0.0 | 5.0 | 0.0 | 2.0 | 0.0 | 0.5 | 0.0 |
| Total | 35 | 8.0 | 4.2 | 0.0 | 30 | 0.0 | 10 | 0.0 |
| Mean | 3.5 | 0.8 | 4.2 | 0.0 | 3.0 | 0.0 | 1.0 | 0.0 |
| Efficacy | | 60% | | 100% | | 100% | | 100% |

EXAMPLE VII

CRYPTOSPORIDIUM PARVUM

A Phase II clinical trial was recently completed with AIDS patients who had Cryptosporidial diarrhea and failed to respond to other therapies. The results showed that 58 percent had a clinical response, with 50 percent having complete or partial reduction in bowel movement frequency. In addition, interim results of an ongoing Compassionate Use study of NTZ also were positive. NTZ was associated with a significant progressive decrease in the frequency of bowel movements and liquid stools by the end of the first week. Moreover, body weight in these patients increased by approximately one pound per week during eight weeks of therapy.

EXAMPLE VIII

BGC

Nitazoxanide was compared against izoniazide antibiotic. The protocol used BCG (Bacille de Calmette et Guerin) as a mycobacterium strain. The sensitivity of this strain was the same as that of *M. tuberculosis*, but this strain is more harmless and thus did not require high level of containment of a tuberculosis agent.

4 mg/mouse per day in 0.2 ml of sunflower oil was administered to mice. The results in mice treated with nitazoxanide were comparable to the group receiving izoniazide.

| | $10^7$ | | | $10^5$ | | |
|---|---|---|---|---|---|---|
| | Spleen | Liver | Lungs | Spleen | Liver | Lungs |
| Nitazo | 1 575 000 | 1 575 000 | 57 500 | 68 250 | 70 000 | 50 |
| | 800 000 | 1 550 000 | 122 500 | 65 000 | 87 500 | 75 |
| | 875 000 | 1 550 000 | 30 000 | 75 000 | 35 000 | 150 |
| | 950 000 | 750 000 | 75 000 | 60 000 | 60 000 | 50 |
| INH | 475 000 | 1 050 000 | 11 000 | 20 000 | 21 250 | 50 |
| | 255 000 | 750 000 | 5 750 | 15 250 | 27 500 | 125 |
| | 200 000 | 975 000 | 4 000 | 60 000 | 52 500 | 50 |
| | | | | 20 000 | 37 500 | 50 |
| PBS | 1 500 000 | 2 125 000 | 92 500 | 102 500 | 195 000 | 750 |
| | 1 525 000 | 1 800 000 | 98 000 | 140 000 | 175 000 | 800 |
| | 1 925 000 | 1 750 000 | 177 500 | 98 000 | 150 000 | 500 |
| | 1 675 000 | 1 800 000 | 117 500 | 105 000 | 150 000 | 750 |

With respect to the above description then, it is to be realized that the optimum formulations and methods of the invention are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Now that the invention has been described,

What is claimed is:

1. A method for treating an infection in an immunocompromised mammal by a microorganism selected from the group consisting of *Cryptosporidium parvum, Isospora belli, Enterocytzoon bieneusi, Encephalitozoon intestinalis, Mycobacterium tuberculosis, Mycobacterium avium intracellulare, Pneumocystis carinii,* and *Toxoplasma gondii*, the method comprising administration of a pharmaceutical composition containing as active agent at least one compound selected from the group consisting of a compound of formula I:

(I)

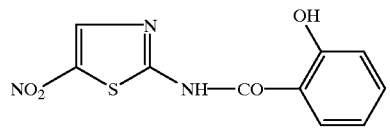

and a compound of formula II:

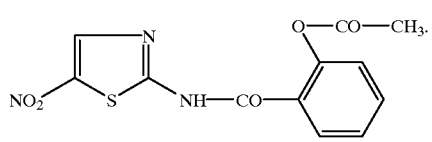
(II)

2. A method as in claim 1, wherein said active agent is in the form of particles with a mean particle size of between 10 and 200 µm.

3. A method as in claim 2, wherein said active agent is in the form of particles with a mean particle size of between 20 and 50 µm.

4. A method as in claim 2, wherein less than 10% of the said solid particles have a particle size larger than 100 µm.

5. A method as in claim 1, wherein said pharmaceutical composition contains at least one pharmaceutically acceptable acid.

6. A method as in claim 5, wherein said pharmaceutically acceptable acid is selected from the group consisting of citric acid, glutamic acid, succinic acid, ethanesulfonic acid, acetic acid, tartric acid, ascorbic acid, methanesulfonic acid, fumaric acid, adipic acid, malic acid and mixtures thereof.

7. A method as in claim 5, wherein the ratio of the weight of pharmaceutically acceptable acid/the weight of said active solid particles is between 0.01 and 0.5.

8. A method as in claim 1, which contains as active agent a mixture of solid particles of compounds of formula I and of formula II, the weight content of compound of formula II with respect to the weight of compounds of formula I and of formula II of said mixture is between 0.5 and 20%.

9. A method as in claim 1, wherein said particles of active agent include a granulating agent selected from the group consisting of polyvinylpyrrolidone, water, alcohol, sucrose hydroxyl cellulose and mixture thereof.

10. A method as in claim 1, wherein said microorganism is *Cryptosporidium parvum*.

11. A method as in claim 1, wherein said microorganism is *Isospora belli*.

12. A method as in claim 1, wherein said microorganism is *Enterocytzoon bieneusi*.

13. A method as in claim 1, wherein said microorganism is *Encephalitozoon intestinalis*.

14. A method as in claim 1, wherein said microorganism is *Mycobacterium tuberculosis*.

15. A method as in claim 1, wherein said microorganism is *Mycobacterium avium intracellulare*.

16. A method as in claim 1, wherein said microorganism is *Pneumocystis carinii*.

17. A method as in claim 1, wherein said microorganism is *Toxoplasma gondii*.

18. A method as in claim 1, wherein said active agent is a compound of formula I.

19. A method as in claim 1, wherein said active agent is a compound of formula II.

20. A method as in claim 1, wherein said immunocompromised mammal is human and wherein said active agent is administered in an amount of from 500–2000 mg daily.

21. A method as in claim 20, wherein said active agent is administered in an amount of from 1000–1500 mg daily.

22. A method as in claim 1, wherein said immunocompromised mammal is a human.

23. A method as in claim 22, wherein said immunocompromised human is a human afflicted with AIDS.

24. A method as in claim 1, wherein said immunocompromised mammal is a mammal receiving immunosuppressive drugs.

* * * * *